United States Patent [19]
Park et al.

[11] Patent Number: 5,571,395
[45] Date of Patent: Nov. 5, 1996

[54] BREATH ALCOHOL ANALYZER USING A BIOSENSOR

[75] Inventors: Je Kyun Park, Seoul; Hee Jin Lee, Kwangmyung-si, both of Rep. of Korea

[73] Assignee: Goldstar Co., Ltd., Seoul, Rep. of Korea

[21] Appl. No.: 334,128

[22] Filed: Nov. 4, 1994

[30] Foreign Application Priority Data

Nov. 4, 1993 [KR] Rep. of Korea ............... 23296/1993

[51] Int. Cl.⁶ .................................................. G01N 27/26
[52] U.S. Cl. .......................... 204/403; 204/406; 204/412; 204/414; 204/415; 435/817; 435/287.7; 435/287.9; 422/83; 422/84; 422/88; 422/90; 422/98
[58] Field of Search .............................. 204/403, 406, 204/414, 412, 415; 435/817, 288, 291; 422/83, 84, 88, 90, 98

[56] References Cited

U.S. PATENT DOCUMENTS

| | | | |
|---|---|---|---|
| Re. 31,915 | 6/1985 | Oswin et al. | 204/403 |
| 4,655,880 | 4/1987 | Liu | 204/1 E |
| 4,678,057 | 7/1987 | Elfman et al. | 180/272 |
| 4,707,336 | 11/1987 | Jones | 422/84 |
| 4,897,173 | 1/1990 | Nankai et al. | 204/403 |
| 4,900,514 | 2/1990 | Fuller | 422/84 |
| 4,905,498 | 3/1990 | O'Donnell et al. | 73/23.1 |
| 4,950,379 | 8/1990 | Young et al. | 204/415 |
| 4,957,705 | 9/1990 | Uchikawa | 422/94 |
| 4,976,135 | 12/1990 | Stock | 73/23.2 |
| 4,993,386 | 2/1991 | Ozasa et al. | 123/417 |
| 5,093,236 | 3/1992 | Gonzales-Prevatt et al. | 435/9 |
| 5,211,827 | 5/1993 | Peck | 204/252 |
| 5,220,919 | 6/1993 | Phillips et al. | 128/635 |
| 5,264,103 | 11/1993 | Yoshioka et al. | 204/403 |
| 5,282,950 | 2/1994 | Dietze et al. | 204/406 |
| 5,312,590 | 5/1994 | Gunasuigham | 422/98 |
| 5,358,765 | 10/1994 | Markulin | 428/34.8 |

Primary Examiner—Bruce F. Bell
Attorney, Agent, or Firm—Finnegan, Henderson, Farabow, Garrett & Dunner, L.L.P.

[57] ABSTRACT

A biosensor for measuring alcohol concentration includes an insulating substrate and an amperometric device formed on the insulation substrate, having a plurality of conductive lines and connective pads and a plurality of electrodes. An enzyme immobilized layer is formed on one of the plurality of electrodes of the amperometric device and an enzyme paste is printed on the amperometric device. An outer membrane is formed on the substrate having the plurality of electrodes for forming an electrode system and an insulating membrane is formed on the substrate, except on the outer membrane.

8 Claims, 4 Drawing Sheets

BREATH ALCOHOL ANALYZER USING A BIOSENSOR

BACKGROUND OF THE INVENTION

The present invention relates to a biosensor which can measure alcohol concentration by reacting with vapor-phase alcohol, a method for manufacturing a strip-type biosensor for measuring alcohol concentration, and a breath alcohol analyzer using the biosensor for measuring alcohol concentration. Conventional biosensors using electrochemical measuring methods have been made by immobilizing, as a membrane, enzymes or microorganisms on the surface of an electrode such as a $H_2O_2$ electrode, an oxygen electrode, an $NH_4^+$ ion selective electrode or of ISFET. Such type of biosensors can detect and measure an electroactive compound formed as the result of a single or multi-step enzyme reaction.

U.S. Pat. No. 4,655,880 disclose a biosensor by which various kinds of oxidase are immobilized on a thick film amperometric electrode to measure an electroactive compounds. However, the biosensor using such electrochemical measuring methods has a drawback in that it should be used in a favorable condition for a biologicial reaction. That is to say, such biosensors can detect only liquid-phase sample.

To overcome such a drawback of the conventional biosensors, a gas measuring biosensor, which can measure a vapor-phase organochemical material, and the method therefor are disclosed in the Korean patent application No. 93-13482. This technology the method for manufacturing a biosensor having a structure in which an sensing membrane having a hydrogel layer on which an enzyme reacting with vapor-phase organochemical material is immobilized on the electrode of an amperometric device. Most breath alcohol analyzers are commercially produced using a gas sensor adopting an oxide semiconductor, e.g., TGS 822 gas sensor manufactured by Figaro Inc. of Japan. Examples of the breath alcohol analyzer include an alcohol checker manufactured by Figaro Inc. of Japan and a breath alert manufactured by Breath Alert MFG of U.S.A. Such breath alcohol analyzer technologies measure alcohol concentration contained in the gases generated during human exhalation in the range from 0.1 mg/l to 0.8 mg/l, and displaying a drinking degree using a light emitting diode (LED). There has also been proposed a technology in which an alert sound is produced if a drinking degree is higher than or equal to a predetermined level.

The ground for measuring the drinking degree is based on an experimental report that alcohol concentration contained in 1 ml blood almost equals to that contained in 2000 ml exhalation, that is, the correlation between alcohol concentration in the exhaled gas and in blood.

Therefore, blood alcohol concentration is indirectly known by measuring alcohol concentration of respired gases after drinking, hence the drinking degree is determinable.

In order to determine a probable drinking and driving which can be a basis for cancelling a driver's license as well as prosecution, there is a need for a sensor for measuring exact alcohol concentration contained in exhaled gases in the range of 20 to 500 ppm.

A method for measuring a drinking degree using an enzymatic reaction is disclosed in the Japanese publication laid-open patent Nos. shows 60-196198 and shows 60-172298. These technologies measure alcohol concentration contained in aqueous solutions, e.g., saliva, using a strip-type test paper, to measure the drinking degree. The international patent WO88/01299 proposes a drinking measuring technology for measuring alcohol concentration contained in gases generated during respiration by the color change of the test paper.

However, there has not yet been proposed a technology for measuring a drinking degree using a biosensor.

The aforementioned conventional technologies for measuring alcohol concentration involve the following problems.

First, the conventional breath alcohol analyzers using an oxide semiconductor gas sensor adopting an alcohol reactive metal oxide such as $SnO_2$, $TiO_2$ or $RuO_2$ have no selectivity for ethanol. That is to say, in general, those breath alcohol analyzers are considerably affected by combustible gases like automobile exhaust, LPG, cigarette smoke, or thinner.

Second, when drinking degrees are intended to be measured consecutively during a short time period, if alcohol concentration for a previous person is strong enough considerably to affect the next person's alcohol concentration, the measurement accuracy decreases. To avoid such an affect from the previous person, those breath alcohol analyzers should be used after a delay of a predetermined time once they are used, which does not allow measurement for many people during a short time period.

Third, the conventional breath alcohol analyzers are readily affected by ambient temperature and have serious measuring errors depending on measuring methods. Thus, the breath need to be calibrated every two or three months.

Fourth, most breath alcohol analyzers require that a person blow a strong breath into the inlet of the sensor for not less than three seconds for measuring the drinking degree. In such a case, saliva may be intermixed into the sensor, which makes the measurement unreliable. Also, the mixed saliva may cause problems for the sensor.

Fifth, since the conventional technology for evaluating the drinking degree using the enzymatic reaction should detect the color change by means of a material such as 2,6-dichloroindophenol, the measured drinking degree may vary depending on the operator, which causes a lack of precision or objectivity in measuring a drinking degree. Further, there is a problem in that another measurement must be performed for more precise measurement of the drinking degree.

Therefore, a portable breath alcohol analyzer using a biosensor for measuring vapor-phase organochemical material according to the present invention solves the following technological problems.

1. In a biosensor using an electrochemical principle, in order to measure a vapor-phase sample, i.e., detectable gas, the sensing membrane of the biosensor should provide an electrode system. The conventionally proposed gas measuring biosensor utilized a hydrogel for measuring a vapor-phase sample.

2. Electrons should be transferred easily between an enzyme layer immobilized on the upper portion of the sensor and the electrode so that sufficient electrical signals are generated during the reaction with the vapor-phase sample. For this purpose, an electrode manufacturing technology, an enzyme technology and the combination of those technologies should be realized.

3. The breath alcohol analyzer using a disposable biosensor should have excellent individual characteristics of the sensors so that the objectivity of the measured values can be secured. Conventionally, the amperometric devices using thick film technology have been manufactured. However, in this case, in order to form an enzyme immobilized layer, since an enzyme solution should be dropped on the upper portion of the sensors individually, mass production is difficult and excellent individual characteristics of the devices cannot be obtained.

4. Since biosensors should be continuously provided separately from the drunkometer, the storage capacity of the biosensors should be sufficient in view of the distribution period of the biosensors.

5. The method for measuring a drinking degree should be simplified using a portable breath alcohol analyzer and biosensor.

SUMMARY OF THE INVENTION

It is an object of the present invention to provide a biosensor and method for measuring alcohol concentration, having a selectivity for ethanol and using an electrochemical principle, which can measure the drinking degree by reacting electrically with vapor-phase alcohol contained in human exhaled gas.

It is another object of the present invention to provide a biosensor and method for measuring alcohol concentration, in which alcohol concentration measured with respect to a previous person does not affect measurement on the next person and accurate measurement can be obtained by preventing saliva or change of ambient temperature from affecting the measurement.

It is still another object of the present invention to provide a biosensor and method that can measure the drinking degree quantitatively, allow mass production, and have excellent individual characteristic.

It is yet another object of the present invention to provide a biosensor and method that can allow a mass production by forming and printing enzyme paste having a constant viscosity such that a thick film amperometric device that can measure electroactive material is manufactured and immobilized enzyme layer is then formed on a working electrode.

It is a further object of the present invention to provide a breath alcohol analyzer using a biosensor having a selectivity for ethanol and using electrochemical principles, that can measure the drinking degree by reacting with vapor-phase alcohol contained in exhaled gas.

It is still a further object of the present invention to provide a breath alcohol analyzer using a biosensor, by which alcohol concentration measured with respect to a previous person does not affect the measurement with respect to the next person and accurate measurement can be obtained by preventing saliva or change of ambient temperatures from affecting the measurement.

It is yet a further object of the present invention to provide a breath alcohol analyzer for measuring a drinking degree precisely, using a biosensor that can measure the drinking degree quantitatively, allow a mass production, and have excellent individual characteristics.

Moreover, it is an object of the present invention to provide a breath alcohol analyzer that can measure a drinking degree by a simple manipulation and treatment, display the measured drinking degree quantitatively, and enhance the objectivity of the drinking degree measurement.

To accomplish the above objects, and in accordance with the purpose of the invention, a biosensor for measuring alcohol concentration comprises an insulating substrate; a thick film amperometric device, formed on the insulation substrate, having a plurality of conductive line and connective pads and a plurality of electrodes; an immobilized enzyme layer formed on one electrode among the plurality of electrodes of the amperometric device, on which an enzyme paste is printed; an outer membrane formed on the substrate having the plurality of electrodes, for forming an electrode system; and an insulating membrane formed on the substrate excluding the outer membrane.

In another aspect, a method for manufacturing a biosensor comprises the steps of manufacturing an enzyme paste forming a thick film amperometric device on an insulating substrate; forming an enzyme immobilized layer by printing the enzyme paste on the amperometric device; and printing and forming an outer membrane on the electrode of amperometric device.

In another aspect, a breath alcohol analyzer using a biosensor comprises a sensor and amplifying circuit for sensing the current generated due to the reaction of the biosensor with alcohol and amplifying the generated current; an analog-to-digital converter for converting a signal output from the sensor and amplifying circuit into a digital signal; a microprocessor for processing the digital signal output from the analog-to-digital converter and turning the same into a drinking degree; and a display for receiving the signal output from the microprocessor and displaying the drinking degree.

In a further aspect, a breath alcohol analyzer using the biosensor comprises a biosensor which reacts with a vapor-phase alcohol sensor; a microprocessor for signal-processing the current detected by the biosensor and converting the processed current into alcohol concentration; a display for displaying alcohol concentration value of the microprocessor; a main body in which the microprocessor and biosensor are installed; a cover connected with the main body by means of a hinge, which can be open or shut; a biosensor placement portion opposed to the cover, for placing the biosensor at the inner surface of the main body; a sample gas inlet formed on the side surface of the cover for blowing a testee's exhalation therein; a sample gas path for guiding the gas passed through the sample gas inlet so as to pass the sensitive portion of the biosensor; and a sample gas outlet for discharging the remaining gas passed through the sample gas path.

DETAILED DESCRIPTION OF THE INVENTION

Figure 1:
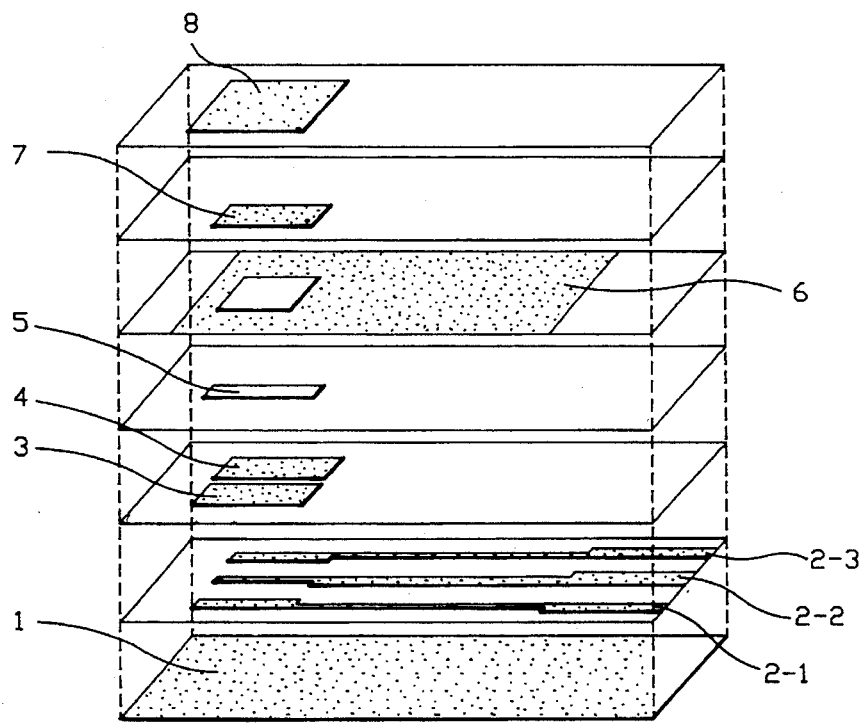
FIG. 1 shows a screen printing process in manufacturing a biosensor according to an embodiment of the present invention.

In the case of a biosensor using an electrochemical measuring method, an electrolyte should exist for measuring a vapor-phase organochemical material. In order to analyze a liquid-phase sample, such as blood, since the salt ion existing in the sample solution functions as an electrolyte, there is no problem in forming an electrode system.

However, a solid electrolyte such as zirconia cannot be used like an enzyme. Also, in the case of forming the electrolyte in a liquid phase, it is very difficult to form the electrolyte on an immobilized enzyme membrane.

For this purpose, the enzyme membrane was conventionally formed by using a hydrogel which can function as a carrier and an electrolyte to the enzyme. However, since this technology has problems in that a constant amount of enzyme solution should be dropped individually on the upper portions of sensors, as described above, it is difficult to achieve excellent reproducibility and mass production.

Therefore, in the present invention, after a carbon paste is used in manufacturing a thick film amperometric device that can measure electroactive material such as 1,4-dihydronico thinamide adenine dinucleotide (NADH), an enzyme paste having a constant viscosity is printed to the thick film amperometer device in such a manner that an enzyme immobilized layer is formed on a working electrode.

Also, in the present invention, a paste having a hydroxyethylcellulose as an outer membrane is manufactured and then printed, thereby improving the effect of absorbing moisture in the sample gas to be measured while using the sensor.

According to this method, when measuring a vapor-phase alcohol, an electrode system can be formed easily only with the moisture contained in the sample gas. Also, the biosensor can be kept in the state of a dry enzyme membrane. Thus, the reduction of enzyme activity can be prevented in keeping the biosensor. In other words, since moisture of about 80 mg is contained in the exhaled gas during a human respiration, the aforementioned method is adopted for measuring alcohol concentration using human exhalation. This eliminates the difficulty of forming an electrode system only with the moisture contained in the sample gas.

Therefore, after dry-packing the biosensor, the biosensor reacts only during measurement, thereby improving its stability for heat and extending its life span. Also, since the signal-to-noise ratio is small, different from the other type of biosensor used in an aqueous phase, and a high enzyme affinity for the vapor-phase organochemical material can be utilized, it is possible to analyze a low concentrated sample, which is difficult to measure in a liquid phase.

Also, carbon is used for a working electrode, which makes the electrode absorption of the enzyme excellent. Enzyme paste composed of carbon powder, high polymers, or enzymes is screen-printed to form an enzyme immobilized layer. Thus, a mass production becomes possible by incorporating the whole process for manufacturing a biosensor into the process for forming a thick film amperometric device, including an enzyme immobilization process.

In the case of utilizing high polymer material such as polyvinyl chloride (PVC), polycarbonate or polyester as an insulating substrate, instead of an alumina substrate, a unit of a sensor device can be manufactured at a low cost. In the present invention, the polyester substrate is used which is excellent for paste adhesiveness for manufacturing electrodes and for printing effect. However, in view of the characteristics of high polymers, a paste which requires a sintering condition of a high temperature of about 800° C. cannot be used. Instead, a high polymer thick film ink is used which exhibits an electrode characteristic only by sintering at about 150° C. or less.

FIG. 1 is a perspective view showing the process for manufacturing a biosensor according to an embodiment of the present invention. The method for manufacturing a biosensor according to an embodiment of the present invention includes the steps of manufacturing an enzyme paste, forming a thick film amperometric device having an electrode on an insulating substrate 1, forming an enzyme immobilized layer 7 by printing the enzyme paste on the amperometric device, and printing and forming an outer membrane 8 on the electrode of the amperometric device.

The step of forming amperometric device includes the steps of screen-printing and forming conductive line and connective pads 2 on the insulating substrate 1, forming an electrode in which current flows on the conductive line and connective pads 2 when it reacts with alcohol in the exhaled gas, and forming an insulating layer 6 on the whole surface of the substrate 1 excluding the electrode.

1. Manufacturing an enzyme paste

In the present invention, carbon powder was used as an enzyme paste material. The diameter of the carbon powder is 5 micron and the purity thereof is 99.9%. Alcohol dehydrogenase extracted from yeast, a protein whose enzyme activity is 400U/mg, is used as an enzyme, and β-nicotinamide adenine dinucleotide (NAD$^+$) is used as a cofactor.

NAD$^+$ of 450 mg and alcohol dehydrogenase of 150 mg are sufficiently mixed with 2% hydroxyethylcellulose of 4.29 ml containing 6% ethylene glycol in a mortar, thereby forming a homogeneous enzyme solution.

Carbon powder of 1.29 g is completely mixed with the homogeneous enzyme solution using a mortar, thereby obtaining an enzyme paste. The obtained enzyme paste is refrigerated.

2. Screen-printing

Referring to FIG. 1, as a substrate, an insulating substrate 1 formed of polyester, having a thickness of about 0.3 mm and a dimension of about 86 mm×84 mm is prepared. Silver (Ag) paste is screen-printed on the insulating substrate 1 and is dried at a temperature of about 110° C. for 10 minutes, thereby forming a plurality of conductive line and connective pads 2-1, 2-2 and 2-3.

The carbon paste is screen-printed and the working electrode 3 and counter electrode 4 formed in parallel on one side of the conductive line and connective pads 2-1 and 2-3. Subsequently, silver (Ag) paste including AgCl is screen-printed, thereby forming a reference electrode 5 on the conductive line and connective pad 2-2 between the working electrode 3 and counter electrode 4.

Dielectric paste is screen-printed on the substrate excluding the portion on which an outer membrane of the upper portion of the electrode is to be formed and the other side of the substrate, and an ultraviolet ray of about 80 W/cm capacity is irradiated at a velocity of about 9 m/min, thereby forming an insulating layer 6. Accordingly, a thick film amperometric device is completed. In such a process, 20 thick film amperometric devices are obtained on the insulating substrate.

Finally, 6% hydroxyethylcellulose paste is printed on one side of the substrate including the respective electrodes to form an outer membrane 8, thereby obtaining a biosensor.

Figure 2:
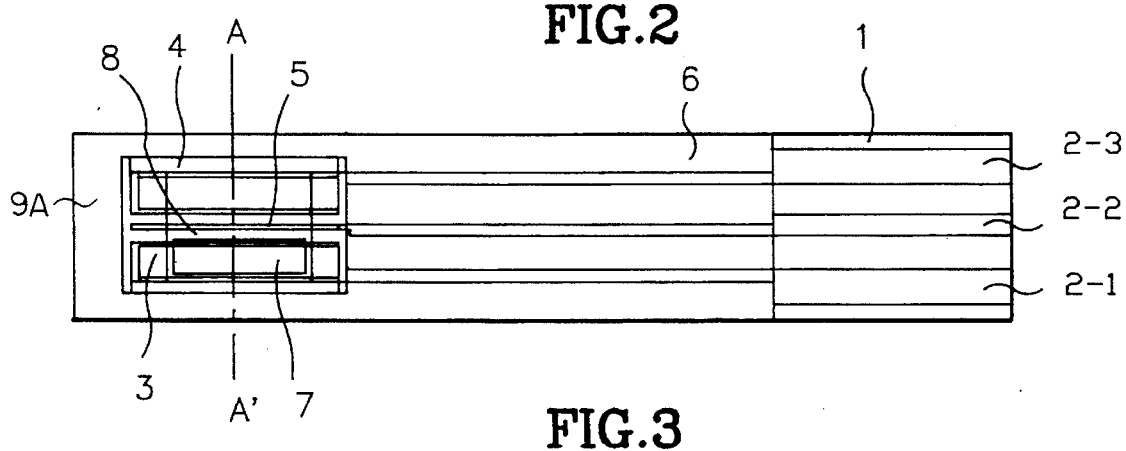
FIG. 2 is a plan view of a biosensor manufactured by the process shown in FIG. 1.
Figure 3:
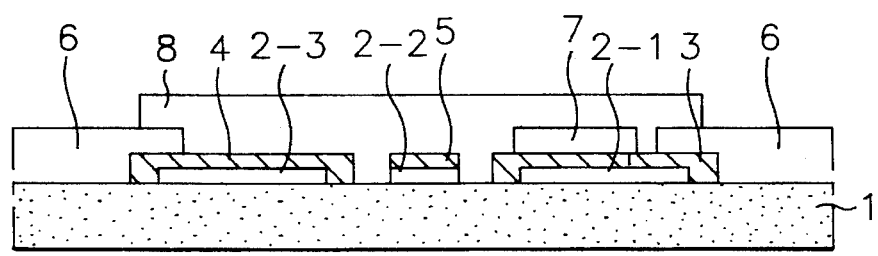
FIG. 3 is a cross-sectional diagram of a biosensor along a line A—A' shown in FIG. 2.

FIG. 2 is a sectional view of a biosensor manufactured in accordance with the aforementioned processes. FIG. 3 is a sectional view along a line A—A' shown in FIG. 2 and shows the sensitive portion of the biosensor. Referring to FIGS. 2 and 3, the biosensor 9 for measuring alcohol concentration includes an insulating substrate 1, a thick film amperometric device formed on the insulation substrate 1, which has a plurality of conductive line and connective pads 2 and a plurality of electrodes 3, 4 and 5, an enzyme immobilized layer 7 formed on one electrode among the plurality of electrodes of the amperometric device, on which an enzyme paste is printed, an outer membrane 8 formed on the substrate having the plurality of electrodes, for forming an electrode system, and an insulating layer 6 formed on the substrate excluding the outer membrane 8.

The amperometric device has a configuration in which three conductive line and connective pads 2 are formed in parallel on the insulating substrate 1, a working electrode 3 and a counter electrode 4 are formed on one side of the substrate on which first and third conductive line and connective pads 2-1 and 2-3 of the plurality of conductive line and connective pads 2-2 are formed, respectively, and a reference electrode 5 is formed on one side of the substrate on which a second conductive line and connective pad 2-2 is formed. At this time, the working electrode 3 and counter electrode 4 are formed so as to have a larger width than the first and third conductive line and connective pad 2-1 and 2-3 which are positioned in the lower portion thereof. The reference electrode 5 is formed so as to have the same width as the second conductive line and connective pad 2-2 which is positioned in the lower portion thereof. The enzyme immobilized layer 7 is formed only on the upper portion of the working electrode 3, as shown in FIG. 3.

Referring to FIG. 2, the sensitive portion 9A of the biosensor is the portion where the working electrode 3, counter electrode 4, reference electrode 5 and enzyme immobilized layer 7 are printed. The respired gas reacts with the sensitive portion 9A, and then current flows corresponding to electrons generated in the sensitive portion 9A. The current flowing between the electrodes is detected, thereby measuring the drinking degree.

3. Packing an ethanol biosensor

As described above, the respective screen-printed sensors are cut and are then airtightly packed, thereby completing the packing of the biosensors. The individual biosensor packed separately is provided for measuring the drinking degree.

The biosensor manufactured by such a series of processes according to the present invention, is evaluated in the following method.

Figure 4:
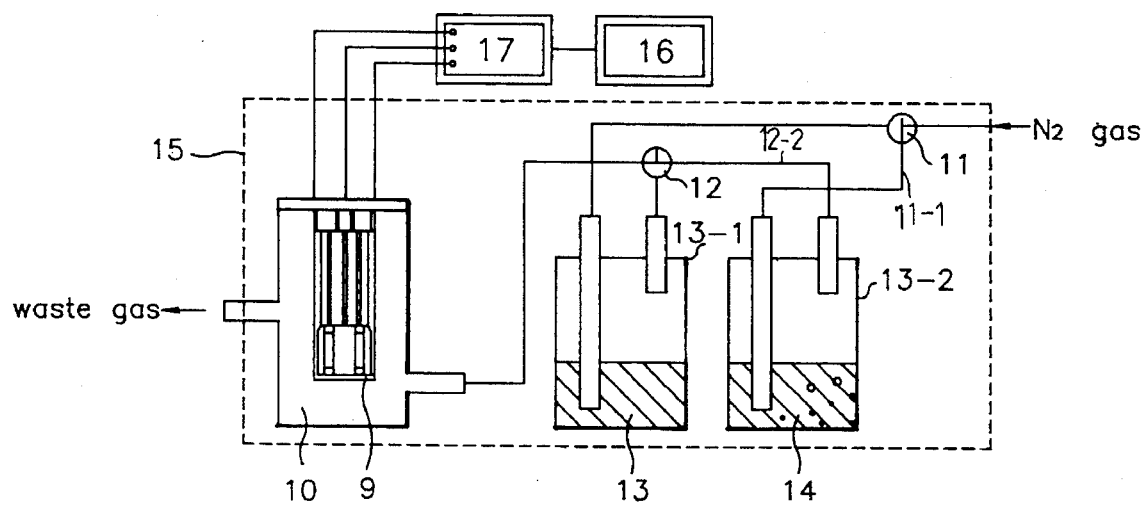
FIG. 4 an example of an apparatus for evaluating the characteristic of a biosensor according to the present invention.

FIG. 4 is a diagram of an apparatus for evaluating the characteristics of the biosensor according to the present invention. Referring to FIG. 4, an apparatus for evaluating the characteristics of the biosensor 9, which evaluates the characteristics of the biosensor using a sample extraction, is placed in a 25 ml measuring cell 10. The apparatus is equipped with two 3-way valves 11 and 12 for controlling the supply path of a nitrogen gas. 0.1M phosphate buffer solution and standard ethanol solution are placed in containers 13-1 and 14-1, respectively. The containers 13-1 and 14-1 are connected to Teflon tubes 11-1 and 12-1 for supplying nitrogen gas, respectively. The measuring cell 10, two 3-way valves 11 and 12, 0.1M phosphate buffer solution 13, and standard ethanol solution 14 are provided in a constant temperature 15.

Also, a constant polarizing voltage between the working electrode and reference electrode of the biosensor 9 is maintained in the measuring cell 10. Potentiostat 17 for detecting the current flowing from the working electrode to the counter electrode and a computer 16 for setting the operational condition of the potentiostat 17, processing the detected information value, and producing the characteristics of the biosensor are provided outside the constant temperature 15.

In the apparatus for evaluating the characteristic of the biosensor according to the present invention, shown in FIG. 4, EG & G manufactured by Princeton Applied Research Corp. is adopted, for example, as the potentiostat 17 for all electrochemical measurements for evaluating the characteristics of the biosensor 9.

The method for evaluating the characteristics of the biosensor using the aforementioned apparatus will now be described.

Biosensor 9 is installed in a 25 ml measuring cell 10 and the temperature of the constant temperature oven 15 is adjusted. Nitrogen gas is passed into the container 13-1 containing 0.1M phosphate buffer solution 13 through the Teflon tube 12-1 at a constant velocity, using 3-way valves 11 and 12, thereby activating the biosensor 9 contained in the measuring cell 10.

Next, the polarizing voltage of the biosensor 9 with respect to the reference electrode made of Ag/AgCl is adjusted to be about 650 mV, using potentiostat 17 connected to the computer 16. Subsequently, nitrogen gas is passed to the container 14-1 containing a constant amount of standard ethanol solution 14 of a predetermined density, using the 3-way valves 11 and 12, thereby making the vaporized ethanol gas react with the biosensor 9. At this time, the concentration of the ethanol gas of the internal measuring cell 10, in which the biosensor 9 is installed, is calibrated by a gas chromatography.

Figure 5:
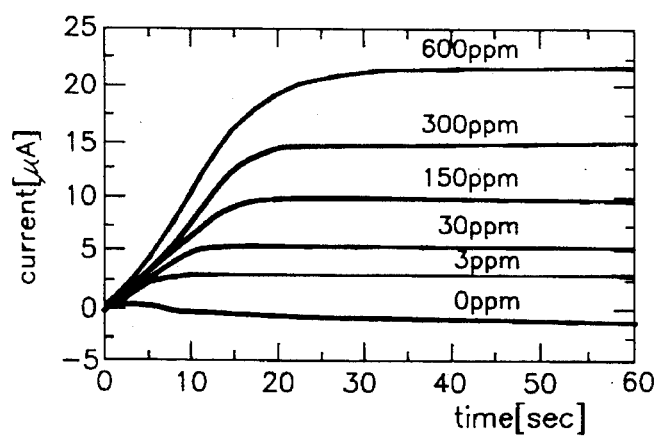
FIG. 5 is a graph showing an ethanol to chronoamperometric responsive characteristic among the characteristics of a biosensor according to the present invention.

As the result of the experiment, the chronoamperometric response for the ethanol gas, which vaporized at a temperature of 25° C., is shown in FIG. 5. Referring to FIG. 3, when the voltage difference is 650 mV, absorption of the ethanol molecules into the enzyme immobilized layer 7 generates an NADH, which is an electroactive material, by action of the immobilized enzyme. The generated NADH is oxidized into $NAD^+$ on the working electrode 3 and current flows from the working electrode 3 to the counter electrode 4 at the same time. At this time, the current flowing from the working electrode 3 to the counter electrode 4 is proportional to the concentration of the ethanol. FIG. 5 shows a graph of time versus the concentration of ethanol. The ethanol concentration can be obtained by using a steady-state current or by measuring an initial rate.

Figure 6:
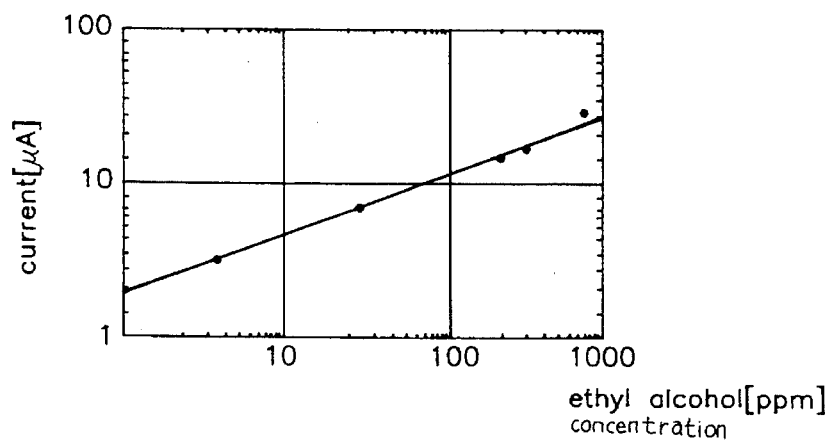
FIG. 6 is a graph showing an ethanol to current between working electrode and counter electrode among the characteristics of a biosensor according to the present invention.

FIGS. 5 and 6 show a standard calibration curve for ethanol concentration obtained by using the steady-state current. Referring to FIG. 6, it is understood that ethanol gas exhibits a good response characteristic in the range between 3 ppm and 600 ppm. Also, the signals having no difficulty in making a module of the biosensor into a device, the sensitivity, and the linear characteristics are excellent. The biosensor having excellent characteristics by meeting the characteristic conditions as described above is used for manufacturing a portable breath alcohol analyzer.

Figure 7:
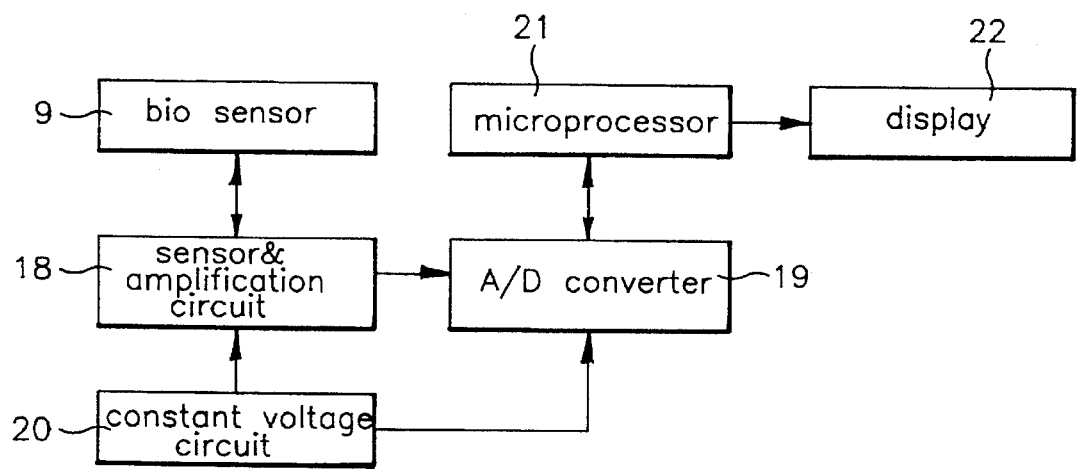
FIG. 7 is a block diagram for showing the circuit of a portable breath alcohol analyzer according to the present invention.

FIG. 7 is a circuit diagram of the breath alcohol analyzer using the biosensor according to the present invention. FIG.

Figure 9:
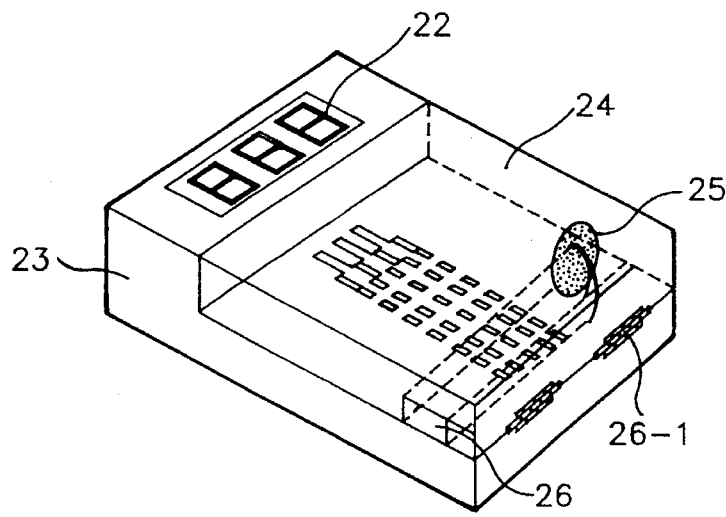
FIG. 9 is a perspective view of a portable breath alcohol analyzer according to the present invention.
Figure 10:
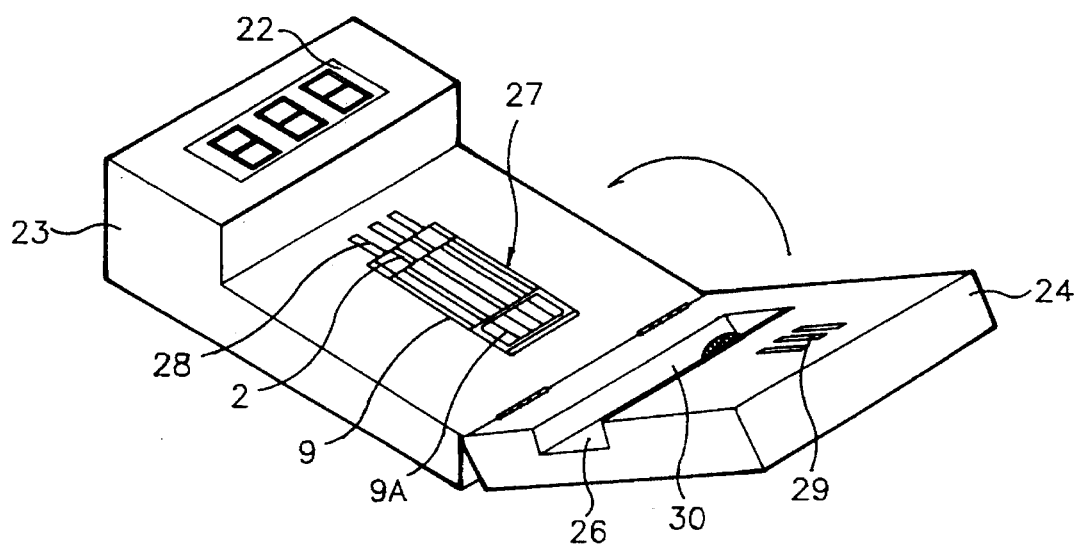
FIG. 10 is a perspective view shown by opening the cover of a portable breath alcohol analyzer according to the present invention.

8 is a detailed circuit diagram of the sensor and amplifying circuit shown in FIG. 7. FIG. 9 is a perspective view of the breath alcohol analyzer, and FIG. 10 is a perspective view of the breath alcohol analyzer when the cover according to the present invention is opened.

Referring to FIG. 7, the breath alcohol analyzer using the biosensor according to the present invention includes a biosensor 9, a sensor and amplifying circuit 18 for sensing the current generated during the reaction of biosensor 9 with alcohol gas and amplifying the same, an analog-to-digital converter 19 for converting the signal generated from the sensor and amplifying circuit 18 to a digital signal, a constant voltage circuit 20 for adjusting the polarizing voltage of the working electrode 3 with respect to the reference electrode 5 on biosensor 9 through the sensor and amplifying circuit 18, a microprocessor 21 for processing the digital signal output from the analog-to-digital converter 19, and converting and outputting the drinking degree, and a display 22 for displaying the drinking degree output from microprocessor 21 as a digital value.

The operation of the breath alcohol analyzer having the aforementioned configuration will now be described.

Constant voltage circuit 20 adjusts the polarizing voltage of working electrode 3 with respect to reference electrodes of biosensor 9 so as to be about 650 mV. When doing so, biosensor 9 reacts with the alcohol gas in a testee's exhalation. The thus generated NADH is oxidized to be $NAD^+$ on working electrode 3 and current flows from working electrode 3 to counter electrode 4 at the same time. The current flowing from working electrode 3 to counter electrode 4 is sensed and amplified by sensor and the amplifying circuit 18, and amplified signal is applied to analog-to-digital converter 19 to be converted to a digital signal.

Analog-to-digital converter 19 converts the input signal for measuring the drinking degree to apply the signal to microprocessor 21. Microprocessor 21 processes the input digital signal for measuring the drinking degree. Display 22 inputs the processed signal from microprocessor 21 and displays the ethanol concentration as a digital value.

Figure 8:
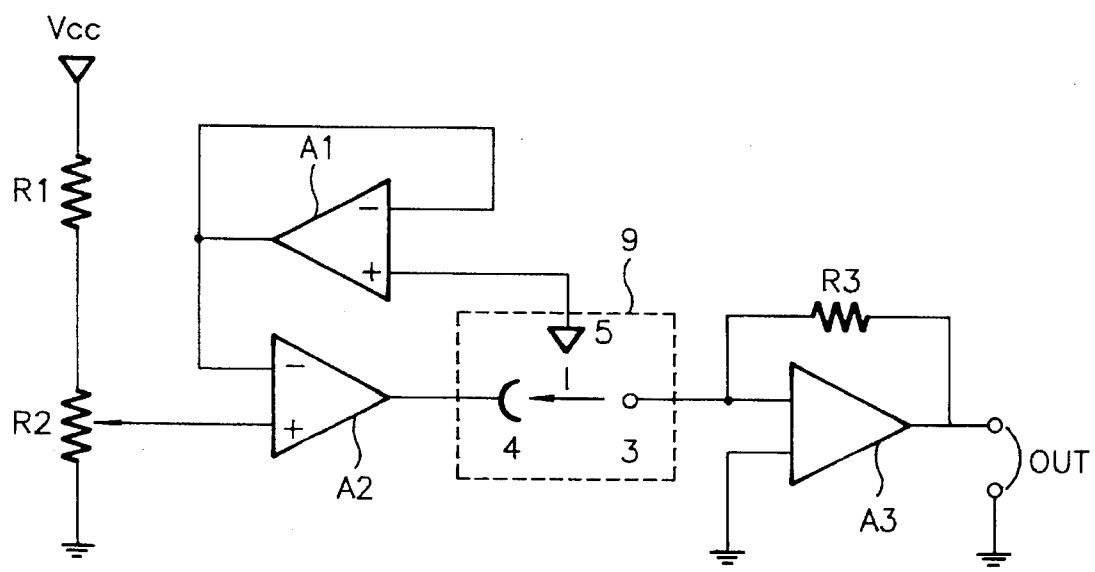
FIG. 8 is a detailed diagram of a sensor and amplifying circuit in the portable breath alcohol analyzer shown in FIG. 7.

The operation of sensing and amplifying the current flowing between the electrodes of the biosensor 9 depending on the ethanol concentration will be described in detail with reference to the detail diagram of sensor and amplifying circuit 18 shown in FIG. 8.

In the sensor and amplifying circuit 18, the constant voltage applied from the constant voltage circuit 20 is distributed by resistance R1 and applied to a non-inverted port (+) of an operational amplifier A2. The output signal of operational amplifier A2 is fed back via biosensor 9 and operational amplifier A1 and applied to an inverted port (−), thereby adjusting the electric potential of working electrode 3 with respect to reference electrode 5 of the biosensor 9 to about 650 mV. In the state where the differential of electric potential is adjusted, biosensor 9 reacts with the alcohol gas contained in the testee's exhalation. While the NADH generated in reacting with ethanol is being oxidized to be $NAD^+$ on working electrode 3, current flows from working electrode 3 to counter electrode 4. The current I flowing from working electrode 3 to counter electrode 4 is amplified via an operational amplify A3 depending on the gain determined by resistance R3 and output to an output port OUT.

The value of the current amplified and output from sensor and amplifying circuit 18 represents an ethanol concentration, i.e., a measured signal of the drinking degree. This signal is supplied to the analog-to-digital converter 19 so that the drinking degree is displayed via display 22, as described above.

An example of realizing the breath alcohol analyzer having the aforementioned circuit configuration is described in FIGS. 9 and 10. Referring to FIG. 9, the breath alcohol analyzer according to the present invention is provided with a display 22 on its main body 23 and the display 22 includes a 7-segment display advice for the easy reading of the drinking degree. Also in the main body 23 of the breath alcohol analyzer, a cover 24 which is connected to the main body 23 by means of a hinge 26-1, is provided which may be opened or closed. A sample gas inlet 25 exposed outwardly is formed on the whole surface of cover 24, thereby enabling the testee to blow in respired gas to measure the drinking degree. Sample gas outlet 26 is formed at the side of cover 24 for exhausting the remaining gas after the biosensor 9 in the main body 23 of the breath alcohol analyzer reacts with the exhaled gas blown through sample gas inlet 25.

FIG. 10 is a perspective view of the breath alcohol analyzer when its cover 24 is opened. If the cover 24 is open, a biosensor placement portion 27 is shown for placing biosensor 9 on the location shut by the cover 24 of the main body 23. On one side of biosensor placement portion 27, a biosensor connective pad 28 for electrically connecting with biosensor 9 is formed. Another biosensor connective pad 29 contacting with biosensor connective pad 28 is located inside the cover 24. When the cover is shut, the two pads contact each other, thereby turning on the power switch of the breath alcohol analyzer.

Also, sample gas path 30 for exhausting the human respired gas blown through sample gas inlet 25 is formed inside the cover 24. Sensitive portion 9A of biosensor 9 is located at about the middle of the sample gas path 30, thereby reacting with alcohol in the sample gases.

Therefore, when the drinking degree is measured by means of the breath alcohol analyzer, the individually packed biosensor is first opened and the cover 24 of the breath alcohol analyzer is opened later to place the opened biosensor 9 on the biosensor placement portion 27. At this time, the placement is performed such that sensitive portion 9A of biosensor 9 is placed on sample gas path 30, and the cover 24 is closed.

If cover 24 is shut, the biosensor connective pad 29 on the cover 24 contacts the biosensor connective pad 28 main body 23 and thus, the power switch of the drunkometer is turned on at the same time. That is to say, as shown in FIG. 7, power is supplied from constant voltage circuit 20 so that the current reacting with alcohol gas of biosensor 9 becomes detectable In such a state, if the testee's exhaled gas is blown into sample gas inlet 25, the respired gas reacts with sensitive portion 9A of biosensor 9 while passing through sample gas path 30 and the remaining gas is exhausted out via sample gas outlet 26.

The reaction of sensitive portion 9A generates a current proportional to the ethanol concentration on the electrodes of biosensor 9, as described with reference to FIGS. 7 and 8. The generated current is calculated to be the testee's drinking degree through various signal processes, as described above, and displayed in display 22. The operator identifies the drinking degree displayed on display 22, thereby discerning alcohol concentration.

Figure 11:
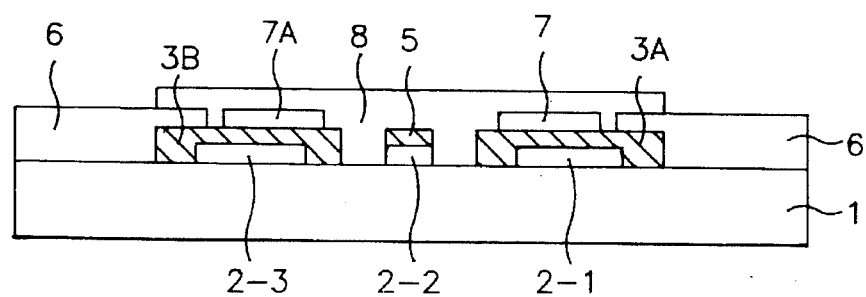
FIG. 11 is a cross-sectional diagram of a biosensor according to an embodiment of the present invention.

FIG. 11 is a diagram of the biosensor according to another embodiment of the present invention. In this embodiment, two working electrodes 3A and 3B are formed, and response interference, i.e., temperature change, except enzymatic reactions may be prevented by using a differential amplifier. In other words, in the biosensor according to the first embodiment described in FIG. 1, since the sizes of working electrode 3 and counter electrode 4 are the same, working electrode 3 and counter electrode 4 are used as two working electrodes 3A and 3B. Also, the value of current reacting with alcohol, shown on the respective electrode, is detected by means of a differential amplifier. Thus, the causes of response interference, i.e., temperature change, other than enzymatic reactions, are prevented, and the sensitivity of output signals can be improved.

At this time, enzyme immobilized layer 7 is formed only on one working electrode 3A, and a layer from which enzyme activity is removed is printed and formed on the other working electrode 3B. Other processes are the same as those in the first embodiment.

By the biosensor according to another embodiment of the present invention, the alcohol concentration contained in an aqueous solution, e.g., saliva or blood, can be measured. However, for alcohol concentration in blood after drinking, the response interference may be caused by an electroactive material other than NADH, such as ascorbic acid present in blood. This is because ascorbic is oxidized at the electric potential of 650 mV, which is required for the oxidation of NADH.

To overcome such a phenomenon, an electron mediator is absorbed on the carbon working electrode so that the electrochemical regeneration of NADH can be easily achieved, or is bonded with aqueous high polymers and used for printing enzyme immobilized layer, thereby enabling operation of electrodes at a low electric potential. Thus, the response interference due to other electroactive materials present in blood can be prevented, and electricity consumption can be saved as well.

According to the present invention as described above, the below-mentioned effects can be achieved.

First, the present invention provides (a) a biosensor that can measure alcohol concentration by reacting with vapor-phase alcohol, (b) a method for manufacturing the strip-type biosensor for measuring alcohol concentration, and (c) a breath alcohol analyzer using the biosensor for measuring alcohol concentration.

Second, since the breath alcohol analyzer using the biosensor can measure the drinking degree accurately after drinking, the objectivity in measuring the drinking degree can be secured, as compared to that using the conventional gas sensor.

Third, since the whole process for manufacturing the biosensor according to the present invention, including the enzyme immobilized layer, can be performed utilizing those for forming an amperometric device, it is advantageous to produce a large volume of biosensors.

Fourth, an electric system can be provided easily only with moisture contained in the sample gas in measuring gases. Also since the biosensors are packed individually, it is possible for biosensors to react with a vapor-phase sample only during measurement of the drinking degree. Thus, the stability for heat is improved and life span thereof becomes long. Also, the signal-to-noise ratio becomes less than those for biosensors used in an aqueous solution.

Fifth, since a high enzyme affinity for a vapor-phase organochemical material can be used, it is possible to measure the drinking degree with a lower concentrated sample.

What is claimed is:

1. A breath alcohol analyzer for measuring alcohol concentration comprises:

a biosensor for reacting with a vapor-phase alcohol gas, the biosensor including:
an insulating substrate,
an amperometric device formed on the insulation substrate and having a plurality of conductive lines and connective pads and a plurality of electrodes,
an enzyme immobilized layer formed on one of the plurality of electrodes of the amperometric device,
an outer membrane formed on the substrate having the plurality of electrodes for forming an electrode system, and
an insulating membrane formed on said substrate except on the outer membrane;

a sensor and amplifying circuit for sensing current generated from the reaction of the biosensor with the alcohol gas and amplifying the current;

an analog-to-digital converter for converting a signal output from said sensor and amplifying circuit to a digital signal;

a microprocessor for processing said digital signal output from said analog-to-digital converter and determining a drinking degree corresponding to the digital signal, the microprocessor outputting a signal indicating the drinking degree; and a display for receiving the signal output from the microprocessor and displaying the drinking degree.

2. A breath alcohol analyzer for measuring alcohol concentration as claimed in claim 1, wherein said plurality of electrodes include a working electrode, a counter electrode and a reference electrode.

3. A breath alcohol analyzer for measuring alcohol concentration as claimed in claim 1, wherein said plurality of electrodes include two working electrodes and a reference electrode.

4. A breath alcohol analyzer for measuring alcohol concentration as claimed in claim 1, wherein said enzyme immobilized layer includes a polymer material, an enzyme, and a cofactor.

5. A breath alcohol analyzer for measuring alcohol concentration as claimed in claim 4, wherein said polymer material includes a carbon powder and hydroxyethylcellulose.

6. A breath alcohol analyzer for measuring alcohol concentration as claimed in claim 4, wherein said enzyme includes an alcohol dehydrogenase.

7. A breath alcohol analyzer for measuring alcohol concentration as claimed in claim 4, wherein said cofactor includes $NAD^+$.

8. A breath alcohol analyzer for measuring alcohol concentration as claimed in claim 1, wherein said outer membrane includes a hydroxyethylcellulose.

\* \* \* \* \*